United States Patent [19]

Werner

[11] Patent Number: 4,908,323
[45] Date of Patent: Mar. 13, 1990

[54] METHOD FOR THE DETERMINATION OF ORGANIC PEROXIDES IN ORGANIC SOLUTIONS

[75] Inventor: Wolfgang Werner, Münster, Fed. Rep. of Germany

[73] Assignee: Merck Patent Gesellschaft Mit Beschränkter Haftung, Darmstadt, Fed. Rep. of Germany

[21] Appl. No.: 121,570

[22] Filed: Nov. 16, 1987

Related U.S. Application Data

[63] Continuation of Ser. No. 586,490, Mar. 5, 1984, abandoned.

[30] Foreign Application Priority Data

Mar. 5, 1983 [DE] Fed. Rep. of Germany ....... 3307907

[51] Int. Cl.$^4$ ............................................. G01N 21/78
[52] U.S. Cl. ..................................... 436/135; 436/66; 436/164; 436/904
[58] Field of Search ................. 436/66, 135, 164, 904; 502/172

[56] References Cited

U.S. PATENT DOCUMENTS 3,873,587  3/1975  Rosenthal et al. .............. 502/160 X
4,173,521  11/1979  Wade ............................. 502/172 X

FOREIGN PATENT DOCUMENTS 0856541  8/1981  U.S.S.R. ............................... 502/172

OTHER PUBLICATIONS

Wolfe, Anal. Chem., vol. 34, No. 10, pp. 1328–1330, 1962.
CRC Handbook of Chemistry and Physics, 62nd Edition, Edited by Weast, CRC Press, Inc., 1981.
Pobiner, Anal. Chem., vol. 33, No. 10, pp. 1423–1426, 1961.
Matsubara et al., Chemical Abstracts, vol. 95, Abstract No. 95:218931n, 1981.
Ferrier et al., J. of Dairy Science, vol. 53, No. 5, pp. 598–599, 1970.
Amin et al., J. of Dairy Science, vol. 50, No. 4, pp. 461–464, 1967.
Siddiqi et al., Chemist Analyst, vol. 44, No. 2, p. 52, Jun., 1955.
Takayama et al., Analytical Abstracts, vol. 3, No. 3, Abstract No. 1083, Mar., 1956.
Sato et al., Chemistry Letters, No. 10 pp. 1469–1472 (1981).
McFarlane et al., Chemical Abstracts vol. 79 No. 141473z (1973).
Kats et al., Chemical Abstracts, vol. 94, No. 94:162836v (1979).
Brilkina et al., "Reactions of Organometallic Compounds with Oxygen and Peroxide" ILIFFE Books Ltd., pp. 164–173 (1969).
"The Peroxide System", E. Merck, Darmstadt, Federal Republic of Germany.
Sichere Chemiearbiet, Aug. 1985, p. 95.
Houben-Weyl, Methoden der Organischem Chemie, vol. II, pp. 568, 574 (Verlag, 1953).
Johnson et al., The Determination of Organic Peroxides, Chapter 6, pp. 43–55 (Pergamon, 1970).
Mair et al., Chapter VI of Swern, Organic Peroxides, vol. II, pp. 535–536, 548, 623, (Wiley & Sons, 1971).

*Primary Examiner*—Robert J. Hill, Jr.
*Attorney, Agent, or Firm*—Millen & White

[57] ABSTRACT

A peroxide-testing method using a reagent based on Ti(IV) compounds which contains, in a lower aliphatic alcohol having 1–5 C atoms, a compound TiX$_4$ in which X is Cl or OR with R being an alkyl group having 1–5 C atoms, and where appropriate, up to 35% by weight of an acid which has a pK$_a$ value not exceeding 5. The method is useful for the determination of peroxides in both aqueous and organic solutions since the reagent is miscible with the sample solution to produce a homogeneous phase.

10 Claims, No Drawings

METHOD FOR THE DETERMINATION OF ORGANIC PEROXIDES IN ORGANIC SOLUTIONS

This application is a continuation, of application Ser. No. 586,490, filed Mar. 5, 1984, now abandoned.

BACKGROUND OF THE INVENTION

The invention relates to a new reagent based on titanium(IV) compounds and a procedure for the determination of peroxides both in aqueous and in organic solutions.

Reagents and procedures for the qualitative or quantitative determination of peroxides in aqueous solutions are known. Odometric determinations using acid solutions of potassium iodide, determinations using the vanadium/sulphuric acid reagent known under the name of the Jorissen reagent, the titanium/sulphuric acid reagent and the titanium tetrachloride/hydrochloric acid reagent are customarily use. In general, these conventional reagents are suitable for the determination of hydrogen peroxide or inorganic peroxides which are soluble in an aqueous medium and which liberate hydrogen peroxide under the reaction conditions.

However, there is a great need for a reagent or procedure for the determination of peroxides in organic solutions. Particular importance is attached to peroxides which are produced in an uncontrolled manner by autoxidation in organic solvents. In this respect, exceptional danger and unpredictability are associated with hydroperoxides and polymeric peroxides which are formed in ethers, such as diethyl ether, diisopropyl ether, tetrahydrofuran and dioxane. On distillation of these solvents, these peroxides accumulate, even from an extremely low starting concentration, in the residue from distillation and can give rise to serious explosions. It is advisable, for reasons of safety, to have available a reagent for the accurate qualitative and quantitative determination of these peroxides. Moreover, it is also desirable to be able to determine other organic peroxide compounds, such as hydroperoxides and diperoxides, peracids, peresters and similar peroxy compounds.

However, the known reagents for the determination of peroxides in aqueous solutions are either unsuitable or only suitable in isolated exceptional cases for determinations in organic solutions. On the one hand, most of the conventional reagents have the disadvantage, that their reaction with peroxides is not specific and further that, in particular, polymeric peroxides are not detected. In addition, they frequently exhibit a sensitivity to atmospheric oxygen, and some of them to light as well, and this results in a considerable susceptibility to interference. On the other hand, the additional problem arises, in the determination of peroxides in organic solutions, that these reagents are not miscible with most organic solvents, and therefore two separate phases form. Moreover, decomposition reactions can occur with the solvents, sometimes with the formation of interfering colored decomposition products.

It is true that, in general, quantitative photometric methods are regarded as being very sensitive. However, because of the immiscibility, phase separation must precede photometric determinations of peroxides using the known reagents, and this makes procedures of this type elaborate and involves further sources of error. Because of the disadvantages which have been detailed, procedures of these types are assessed in the literature (see, for example, R. M. Johnson and J. W. Siddiqui: "The Determination of Organic Peroxides", Oxford, 1970) as being of low precision and unreliable. There is express advice against the use, for the determination of organic peroxides, of reagents based on titanium(IV) compounds which utilize the characteristic yellow-orange color of the peroxotitanyl cation, which is formed with hydrogen peroxide, and which are less sensitive to atmospheric oxygen (R. D. Mair and R. T. Hall: "Determination of Organic Peroxides by Physical, Chemical and Colorimetric Methods" in D. Swern: "Organic Peroxides", Vol. II, New York, 1971).

A need therefore continues to exist for a procedure for the determination of peroxides which is equally suitable for both aqueous and organic solutions, and for a generally applicable reagent suitable for use therein.

OBJECTS OF THE INVENTION

One object of the present invention is to provide a procedure which makes it possible to qualitatively and quantitatively determine peroxides in both aqueous and organic solutions and which is accurate and insensitive to interference.

Upon further study of the specification and appended claims, further objects and advantages of this invention will become apparent to those skilled in the art.

SUMMARY OF THE INVENTION

These objects are attained by providing a reagent, suitable for use in determining peroxides in both aqueous and organic solutions, comprising a solution of an effective peroxide-detecting amount of a titanium)IV) compound of the formula $TiX_4$ in a $C_{1-5}$ aliphatic alcohol solvent, wherein X is Cl or OR, R being a $C_{1-5}$ alkyl group, and wherein the solution also may contain up to about 35% by weight, relative to the total weight of the solution, of an acid have a $pKa \leq 5$.

In a method of use aspect, the invention provides a procedure for determining peroxides, comprising admixing a test solution with an amount of the Ti(IV) reagent of the invention sufficient to determine the presence and/or the amount of peroxides therein, the reagent being miscible with the sample solution to produce a homogeneous phase, and correlating the resultant color with a standard, thereby effecting a qualitative and/or quantitative determination of the peroxide level.

DETAILED DISCUSSION

It has been found, surprisingly, that a reagent based on titanium(IV) compounds, which contains a compound $TiX_4$, in which X is Cl or OR with R being an alkyl group having 1-5 C atoms, dissolved in a lower aliphatic alcohol having 1-5 C atoms with, where appropriate, the addition of an acid having a $pKa \leq 5$, is suitable in an outstanding manner for the determination of peroxides in both aqueous and organic solutions, it being miscible with the sample solution to produce a homogeneous phase.

The reagent according to the invention contains, as the active substance, a compound $TiX_4$ in which each X is independently Cl or OR, R being an $C_{1-5}$ alkyl group, e.g., titanium tetrachloride or a tetraalkyl orthotitanate, such as tetramethyl, tetraethyl, tetra-n-or -i-propyl, tetra-n-, -i-, -t-butyl or tetra-n-pentyl orthotitanate. The compounds titanium tetrachloride, tetraethyl orthotitanate, tetra-n-propyl orthotitanate and tetra-i-propyl orthotitanate are preferred.

These titanium compounds are soluble in aqueous and organic media. Their function is to provide, under the conditions of the determination, dissolved $Ti^{4+}$ to form with peroxides the characteristically colored peroxotitanyl cation which is used for the determination.

The reagent according to the invention contains as the solvent one or more aliphatic alcohols having 1–5 C atoms. Suitable such alcohols include, methanol, ethanol, n-propanol or isopropanol, n-butanol, n-pentanol or isoamyl alcohol. Methanol, ethanol, n-propanol and isopropanol are preferred.

To a large extent, the concentration of the titanium compound in the reagent solution according to the invention is not crucial. Solutions which contain up to about 10%, preferably 0.5–5%, more preferably about 1% by weight of titanium compound have proved to be advantageous. However, it is possible to use solutions of various concentrations for specific uses, and these can readily be optimized by simple testing in each particular case.

It is possible for the reagent according to the invention to contain an added acid which has a $pK_a$ value not exceeding 5. This is necessary when the intention is to determine peroxides which only form hydrogen peroxide in an acid medium.

When the reagent contains titanium tetrachloride, addition of acid is unnecessary, although a small amount may be advantageous because hydrochloric acid is produced in the reagent by alcoholysis of this compound. In other cases, the added acid can be up to 35%, e.g., 5–5%, preferably about 10%, by weight relative to the total amount of the reagent.

To a large extent, the nature of the acid which is added is likewise not crucial. With the exception of phosphoric acid and hydrofluoric acid, which adversely affect the determination by reacting with the titanium compound, virtually all inorganic and organic acids which have a $pK_a$ value not exceeding 5 are suitable. Illustrative acids include hydrochloric acid, sulphuric acid, perchloric acid, formic acid, acetic acid, trichloroacetic acid, trifluoroacetic acid, oxalic acid, methanesulphonic acid and p-toluenesulphonic acid. Sulphuric acid, perchloric acid and p-toluenesulphonic acid are preferred. However, it is possible for the expert to find, by simple testing, the optimum composition with respect to the nature and amount of the acid which is added for the particular case.

Preparation of the reagent according to the invention is completely straightforward and considerably simpler than the preparation of the titanium/sulphuric acid reagent which has customarily been used in the art (R. Criegee in Houben-Weyl, Volume II, pages 568–574, Stuttgart, 1953). It is carried out by simply mixing or dissolving the titanium compounds and, where appropriate, the acid in one of the alcohols mentioned.

Because they are completely or largely insensitive to air and temperature effects, the reagents according to the invention are stable and usable for a long time when properly handled and stored.

The procedure according to the invention for the determination of peroxides in aqueous and organic solutions is carried out by admixing about 1–2 ml of the reagent according to the invention with a sample of a few milliliters of the solution to be investigated for peroxides. The case both of aqueous and organic sample solutions, it is possible for this mixture to produce a homogeneous phase. In individual cases, it may be necessary to add a further small amount of one of the alcohols mentioned in order to produce a completely homogeneous phase.

The color appearing in the presence of peroxides is used for qualitative determination.

This can be extended to semiquantitative determination by comparison of the intensity of color obtained with that of standardized comparison solutions which can be prepared by reacting the reagent with aqueous solutions of hydrogen peroxide which contain, for example, 25, 50, 100, 250, 500 etc. mg of $H_2O_2$ per liter. Comparison solutions of this type are stable for a few days.

Accurate quantitative determination of the content of peroxide in the sample solution can be carried out by photometric measurement and determination of the molar extinction. Because of the differences in reactivity of the various peroxides, the quantitative result is advantageously found using a calibration curve which can be obtained by maintaining constant reaction and measurement conditions and using standardized sample solutions. It is not absolutely necessary that the reaction between the peroxide in the sample to be measured and the reagent has gone to completion, since, under the standardized measurement conditions, the proportion of the content of peroxides which has reacted always provides the same intensity of color.

Using the procedure according to the invention, all inorganic and organic peroxides which liberate hydrogen peroxide under the test conditions can be determined in both aqueous and organic solutions. Possible examples of inorganic peroxides are: free hydrogen peroxide, metal peroxides and inorganic peracids or their salts. Examples of organic peroxides are primary, secondary and polymeric ether peroxides, such as those produced or present as explosive autoxidation products in virtually all ethers which are customarily used as solvents; also aliphatic and aromatic hydroperoxides and diperoxides, and peracids, their salts and esters. The fact that the determination of the uncommonly dangerous ether peroxides is simple and reliable makes this procedure especially valuable in practice.

The procedure according to the invention is, reliable, accurate and largely insensitive to possible interference when properly carried out. In principle, care only has to be taken that the sample solutions do not have intrinsic colors which interfere, and do not give rise, to colored by-products which interfere. However, the latter can readily be established by blank tests.

Under certain circumstances, a relatively high concentration of chloride ions in the sample solution can interfere with the determination, since this gives rise to chlorotitanium(IV) complexes which have yellowish colors.

The presence of copper(II) and chloride ions gives rise to chlorocopper(II) complexes which are colored yellow to yellow-orange, such as when ethers have been pretreated with copper(II) chloride and copper powder to remove peroxides by the process in German patent specification No. 3,046,148. It is straightforward to eliminate this possible source of interference by brief treatment of the sample solution with a small amount of a commercial basic ion exchanger The reagent and procedure according to the invention thus make it possible reliably to determine, qualitatively and quantitatively, any peroxide compounds in both aqueous and organic solutions.

Without further elaboration, it is believed that one skilled in the art can, using the preceding description, utilize the present invention to its fullest extent. The following preferred specific embodiments are to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

1 ml of $TiCl_4$ is dissolved in 60 ml of methanol, and the solution is made up to 100 ml with methanol.

1 ml of this solution gives an intensely yellow-orange homogeneous solution with one drop of a 0.3% solution of hydrogen peroxide.

EXAMPLE 2

1 ml of $TiCl_4$ is dissolved in 60 ml of isoamyl alcohol, 10 ml of concentrated sulphuric acid are added, and the solution is made up to 100 ml with isoamyl alcohol.

2 ml of this solution give a homogeneous, yellow-colored solution with 0.2 ml of a solution of diethyl ether hydroperoxide in diethyl ether.

EXAMPLE 3

1 g of $Ti(OC_2H_5)_4$ is dissolved in about 60 ml of ethanol, 10 ml of concentrated sulphuric acid are added, and the solution is made up to 100 ml with ethanol.

EXAMPLE 4

As Example 3, but with 10 ml of formic acid.

EXAMPLE 5

As Example 3, but with 10 ml of acetic acid.

EXAMPLE 6

As Example 3, but with 10 ml of trichloroacetic acid.

EXAMPLE 7

As Example 3, but with 10 ml of trifluoroacetic acid.

EXAMPLE 8

As Example 3, but with 10 g of oxalic acid.

EXAMPLE 9

As Example 3, but with 10 ml of methanesulphonic acid.

EXAMPLE 10

As Example 3, but with 10 g of p-toluenesulphonic acid.

2 ml of each of these solutions give homogeneous solutions which are colored yellow or yellow-orange with 0.2 ml of an aqueous solution of hydrogen peroxide or an ethereal solution of hydroperoxides or triacetone triperoxide.

EXAMPLE 11

1 g of $Ti(OC_2H_5)_4$ is dissolved in a mixture of about 70 ml of methanol and 12 ml of concentrated sulphuric acid, and the solution is made up to 100 ml with methanol.

1 ml of this solution produces, with 2 ml of a solution of 200 mg of triacetone triperoxide in 1 liter of diethyl ether, a homogeneous yellow-colored solution, the content of peroxides in which is determined by photometry with light of wavelength 415 nm.

EXAMPLE 12

1 g of $Ti(O-i-C_3H_7)_4$ is dissolved in 50 ml of isopropanol, 12 ml of concentrated sulphuric acid are added, and the solution is made up to 100 ml with isopropanol.

2 ml of commercial peroxide-containing diethyl ether are added to 1 ml of this solution, whereupon a homogeneous yellow-colored solution forms, the content of peroxide in which is determined semiquantitatively or quantitatively by photometric measurement.

EXAMPLE 13

1 ml of a solution from Example 3 is mixed with 1 ml of methanol and 2 ml of commercial peroxide-containing diisopropyl ether. A homogeneous, yellow-orange solution forms, the content of peroxides in which is determined by photometric measurement.

EXAMPLE 14

1 ml of a solution from Example 3 is mixed with 2 ml of methanol and 2 ml of commercial peroxide-containing di-n-butyl ether. A homogeneous, yellow-orange solution is produced, the content of peroxides in which is estimated semiquantitatively by comparison with standardized sample solutions or is determined accurately by photometric measurement.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for determining organic peroxides in organic solutions comprising admixing with a sample consisting essentially of an organic peroxide in an organic solution an amount of a reagent sufficient to effect a qualitative or quantitative determination of peroxides therein, wherein said reagent consists essentially of a solution of an amount of Ti(IV) compound effective to react with peroxides to form a color, said compound having the formula $TiX_4$, in a $C_{1-5}$ alcohol, wherein X is independently Cl or OR, R being a $C_{1-5}$ alkyl group, with the proviso that if said Ti(IV) compound is Ti(OR)$_4$ said reagent solution further comprises less than about 35% by weight, relative to the total weight of the reagent solution, of a substantially non-aqueous acid having a $pK_a$ not more than 5, the reagent being miscible with the sample to produce a homogenous phase; and determining whether any peroxide is present by correlating any resultant color with a standard.

2. The method of claim 1, wherein said reagent contains said acid, the acid being concentrated sulfuric acid, acetic acid, trichloroacetic acid, trifluoroacetic acid, oxalic acid, methanesulfonic acid or p-toluenesulfonic acid.

3. The method of claim 1, wherein said reagent is Cl, methoxy, ethoxy, n-propoxy or isopropoxy.

4. The method of claim 1, wherein said alcohol in said reagent is methanol, ethanol, n-propanol or isopropanol.

5. The method of claim 1, wherein the peroxide to be determined is at least one of an organic peracid, a salt or ester of an organic peracid, an ether peroxide, an aliphatic or aromatic hydroperoxide, or an aliphatic or aromatic diperoxide.

6. The method of claim 1, wherein, in said reagent, the Ti(IV) compound is $Ti(OC_2H_5)_4$, the alcohol is methanol, and the acid is present and is concentrated sulfuric acid.

7. The method of claim 6, wherein the organic peroxide is triacetone triperoxide.

8. The method of claim 1, wherein, in said reagent, the alcohol is isopropanol, n-butanol, n-pentanol or isoamyl alcohol.

9. The method according to claim 1, wherein the organic solution containing said peroxide is an ether.

10. The method according to claim 9, wherein ether is diethyl ether, diisopropyl ether of di-n-butyl ether.

* * * * *